(12) United States Patent
Russum

(10) Patent No.: US 6,905,300 B1
(45) Date of Patent: Jun. 14, 2005

(54) SLIDE FEEDER WITH AIR BEARING CONVEYOR

(75) Inventor: William C. Russum, Tucson, AZ (US)

(73) Assignee: DMetrix, Inc., Tucson, AZ (US)

( * ) Notice: Subject to any disclaimer, the term of this patent is extended or adjusted under 35 U.S.C. 154(b) by 0 days.

(21) Appl. No.: 10/759,712

(22) Filed: Jan. 16, 2004

(51) Int. Cl.⁷ .................................................. B65G 1/00
(52) U.S. Cl. ...................... 414/331.14; 406/86; 414/676
(58) Field of Search ........................ 414/331.14, 331.18, 414/331.17, 676; 406/86, 88; 221/74, 76, 69, 71

(56) References Cited

U.S. PATENT DOCUMENTS

| | | | | |
|---|---|---|---|---|
| 3,731,823 A | * | 5/1973 | Goth ............................ | 406/88 |
| 3,923,342 A | * | 12/1975 | Shannon ....................... | 406/10 |
| 3,945,505 A | * | 3/1976 | Frisbie et al. ........... | 414/331.14 |
| 4,171,241 A | * | 10/1979 | Henderson et al. .......... | 156/556 |
| 4,744,709 A | * | 5/1988 | Hertel et al. ................ | 414/21 |
| 5,275,521 A | * | 1/1994 | Wada ........................... | 414/404 |
| 5,518,360 A | * | 5/1996 | Toda et al. .................. | 414/755 |
| 6,208,909 B1 | * | 3/2001 | Kato et al. ................... | 700/218 |
| 6,236,904 B1 | * | 5/2001 | Nakamura ................... | 700/218 |
| 6,619,903 B2 | * | 9/2003 | Friedman et al. ....... | 414/331.14 |

* cited by examiner

*Primary Examiner*—Richard Ridley
(74) *Attorney, Agent, or Firm*—Antonio R. Durando; Quarles & Brady Streich Lang LLP

(57) ABSTRACT

A slide loading mechanism utilizes compressed air as the transport medium to move the slides from a magazine to the stage of a microscope. The stage is provided with a carriage moving horizontally along a direct path between the stage and the magazine. A conveyor coupled to the carriage includes a tongue suitable for positioning under the slide of interest in the magazine when the carriage is at one end of its travel path, so that the slide may be picked up for translation to the stage of the microscope. When the carriage is moved to the opposite end of its travel path, the tongue is completely removed from the magazine, which may be freely moved vertically by an elevator to align another slide for processing. Directional air flow is used to suspend and transport the slide back and forth between the two ends of the conveyor

21 Claims, 11 Drawing Sheets

SLIDE FEEDER WITH AIR BEARING CONVEYOR

BACKGROUND OF THE INVENTION

1. Field of the Invention

This invention is related in general to the field of microscopy. In particular, it relates to automated mechanisms to feed slides to a microscope from a removable slide magazine.

2. Description of the Related Art

In pathology and other biomedical practices, a sample is removed from a patient and fixed to a glass slide for staining and microscopic examination. For example, the morphology of the sample is analyzed to provide a qualitative assessment of its condition and to identify the presence of pathologic changes, such as may indicate progression towards a malignancy. For many decades, this visual procedure has been the diagnostic mainstay of pathology.

With the advent of computers and sophisticated digital imaging equipment, researchers have extended the realm of these analytical procedures through the use of mechanized instrumentation for diagnostic and quantitative investigation. In such mechanized procedures, the samples are imaged with a microscope and the images are digitized, stored, and analyzed (so called "virtual slide technology"). Historically, the slides have been stored in horizontal trays that hold 4 to 20 slides. During the process of retrieval and imaging in the microscope, the slides are handled manually.

As digital imaging gains more and more acceptance among pathologists and in laboratories for the purposes of diagnosis, archiving, and telepathology, the transition from conventional to digital procedures is producing a strong need for high throughput in slide digitization. Therefore, an important aspect of the economic viability of virtual slide technology is the ability to process a large number of slides in a short time. The rapid scanning times of ever-improving microscopes need to be accompanied by correspondingly faster and faster automatic slide loading and unloading systems.

Typical slide feeders for projectors and other optical instruments consist of mechanical devices adapted to receive a slide tray or magazine and sequentially retrieve each slide from its slot in the tray or magazine, place the slide on the stage of the instrument for processing, and return the slide to its slot in the tray or magazine. In the field of biomedical imaging, the state of the art consists of a slide loader wherein a tray of slides is first retrieved with a mechanical arm from a stack of trays housed in a library. A slide is lifted with a suction cup from the tray, placed on a microscope stage for processing, and returned to the tray for storage. By sequentially loading and unloading slides from the various trays, the instrument is capable of processing in excess of 100 slides per hour automatically. Such a system is currently sold by Vision Systems Limited of Mount Waverley, Australia, as the SL50 Automated Slide Loader.

While this recent robotic improvement of conventional "pick and place" technology has accelerated the ability to process slides, its performance is limited by the fact that each tray must be removed from a stack prior to retrieval of the slide of interest. In addition, either the tray or the slide needs to be moved vertically for alignment with the elevation of the sample stage. Very sophisticated and relatively cumbersome mechanisms are required to perform such multi-step functions, which is expensive to implement and limits the ability to achieve even greater throughputs. This invention provides a general and efficient solution toward that end.

BRIEF SUMMARY OF THE INVENTION

In view of the foregoing, the invention is described with reference to a generic microscope equipped with a sample stage adapted to receive a conventional glass slide for digital imaging, but it is equally applicable to every situation where a sample slide or equivalent sample carrier needs to be loaded and unloaded automatically from a storage location to a processing stage and back or moved between storage locations. In essence, the invention consists of a slide loading mechanism that utilizes compressed air as the transport medium. According to one aspect of the invention, the glass slides are stored in slots in a vertical magazine that is removably coupled to an elevator adapted to bring each slide in horizontal alignment with the stage of the microscope. Thus, the only motion required for alignment of a slide between successive measurements is the step-by-step vertical translation of the magazine along the axis of the elevator. If desirable, more than one magazine may be connected to the elevator, or mounted on a separate mechanism feeding the elevator, in order to increase the capacity of the device.

According to another aspect of the invention, the stage of the microscope is provided with a carriage adapted to move horizontally along a direct path between the stage and the slide magazine. A slide conveyor coupled to the carriage includes a tongue that is positioned in the magazine slot under the slide of interest when the carriage is at one end of its travel path, so that the tongue may be used to pick up the slide for translation to the stage of the microscope. When the carriage is moved over the stage in optical alignment with the microscope at the opposite end of its travel path, the tongue is completely removed from the magazine, so that the magazine may be freely moved vertically by the elevator to align another slide for retrieval and processing.

One of the main aspects of the invention lies in the use of an air bearing and air flow to suspend the slide over the conveyor and to transport it back and forth between the two ends of the conveyor. Thus, the slide is suspended over the conveyor tongue in the magazine slot and is urged by directional air flow toward the opposite end of the conveyor. In turn, preferably at the same time, the conveyor is transported by the carriage toward the sample stage for positioning of the slide in operational alignment with the objective of the microscope. The procedure is reversed in order to remove the slide from the stage and return it to its slot in the magazine.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The invention was motivated by the fact that the conventional pick-and-place robotic approach to automation is necessarily limited in its effectiveness by the speed and complexity of its mechanisms. Accordingly, the heart of the invention lies in the idea of utilizing air flow both to pick the slides from a storage magazine and to place them over a microscope stage in position for processing. This approach affords grater simplicity of design and operation and, correspondingly, produces materially greater throughputs.

As used herein, the term "plenum" refers to an enclosed space wherein the pressure is greater than the outside atmosphere. The term "runway" is used to designate a substantially horizontal strip along which a slide is moved by air jets, back-and-forth and end-to-end, between a storage position and a processing position, or between different storage or processing positions. A runway may be linear or curved and it may include a transfer structure, such as a turntable, through which a slide is positioned for transport in a different direction or directed toward one of multiple alternative paths within the runway structure. The terms "proximal" and "distal" are used to refer to locations toward the microscope and the magazine, respectively.

Figure 1:
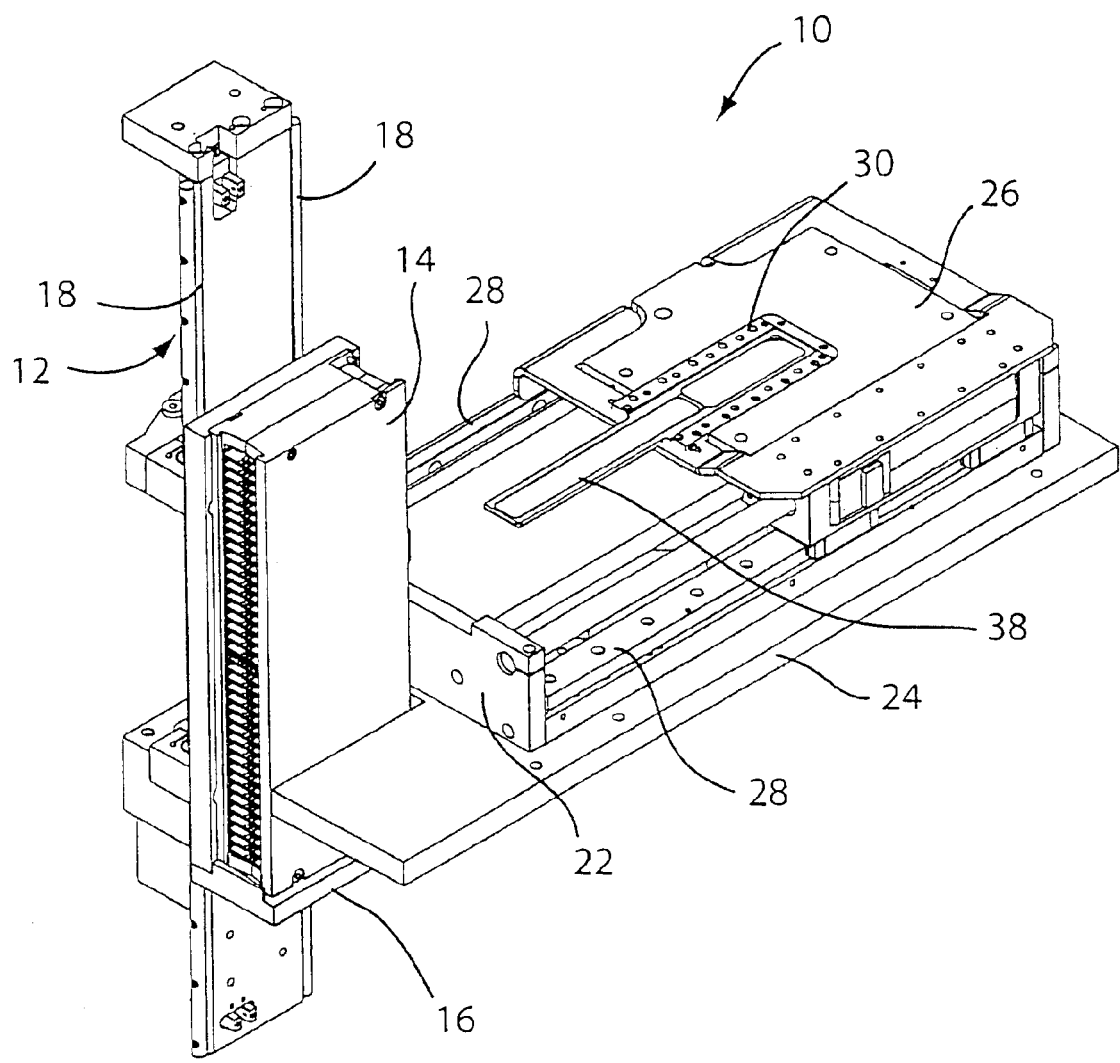
FIG. 1 is a perspective view of a slide feeder according to the invention.

Referring to the drawings, wherein like reference numerals and symbols are used throughout to designate like parts, FIG. 1 is a perspective view of a slide-feeder system 10 according to the invention. In general, the system includes a vertical elevator 12 adapted to receive a slide magazine 14 on a suitable shelf 16. The shelf is slidably mounted on rails 18 and, as shown in the front elevational view of FIG. 2, it is translated vertically by an elevator motor 20 for sequential alignment of the slides in the magazine with the elevation of the sample stage 22 of a microscope (not shown in the figures). A platform 24 rigidly connects the sample stage 22 with the elevator 12.

Figure 2:
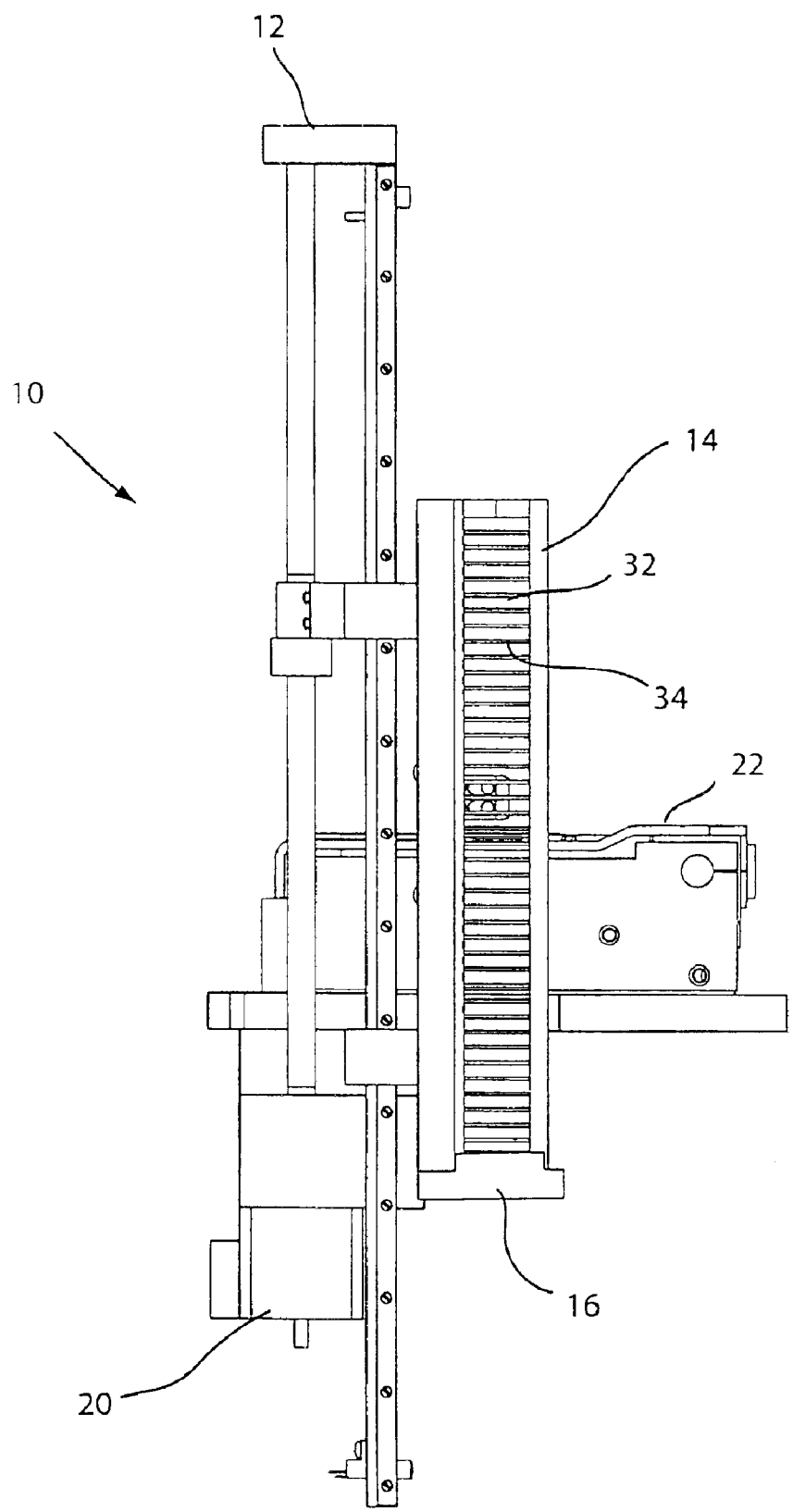
FIG. 2 is a front elevational view of the slide feeder of FIG. 1.
Figure 3:
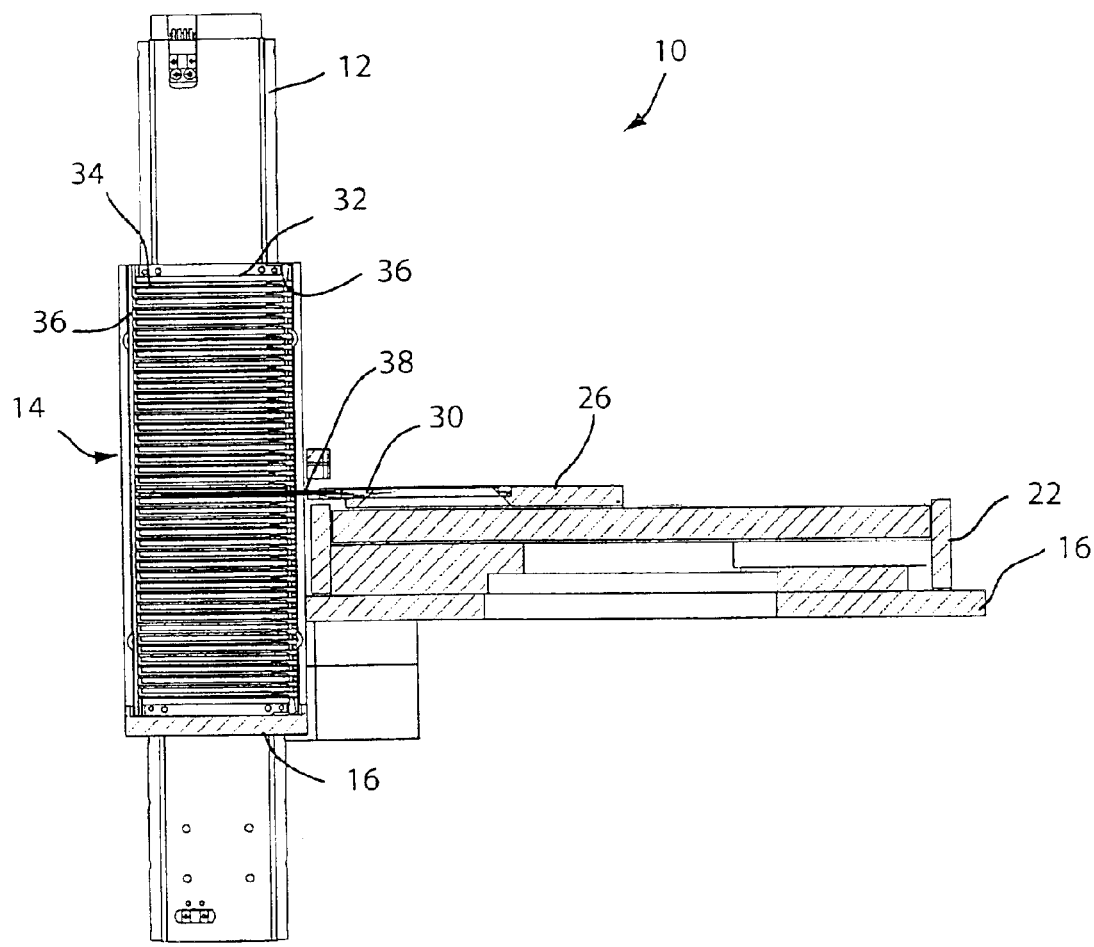
FIG. 3 is a side elevational view of the slide feeder of FIG. 1 illustrating the tongue of the conveyor of the invention placed under a slide in the slot of a storage magazine.

A stage carriage 26 is slidably mounted on the stage 22 such that it can travel over horizontal support rails 28 between a proximal position, wherein the carriage is aligned with the objective of the microscope for processing of a slide, and a distal position wherein the carriage is aligned with the magazine 12 for loading or unloading of the slide. A slide conveyor 30 coupled to the stage carriage 26 serves as the pneumatic transport vehicle for retrieving slides from the magazine 12, moving them into position over the stage 22 for digital imaging, and reloading them into the magazine. As illustrated in FIG. 2 and also in the side elevational view of FIG. 3, the slide magazine 14 includes a plurality of slots 32 adapted to receive a slide 34 suspended by suitable peripheral supports 36, so that the slides may be stacked vertically in the magazine with essentially void spaces between them. The conveyor 30 includes a tongue 38 protruding from the carriage 26 in the direction of the magazine 14 and aligned with the slides so that in the distal position of the carriage the tongue lies underneath the slide to be retrieved from the magazine, as shown in FIG. 3.

Figure 4:
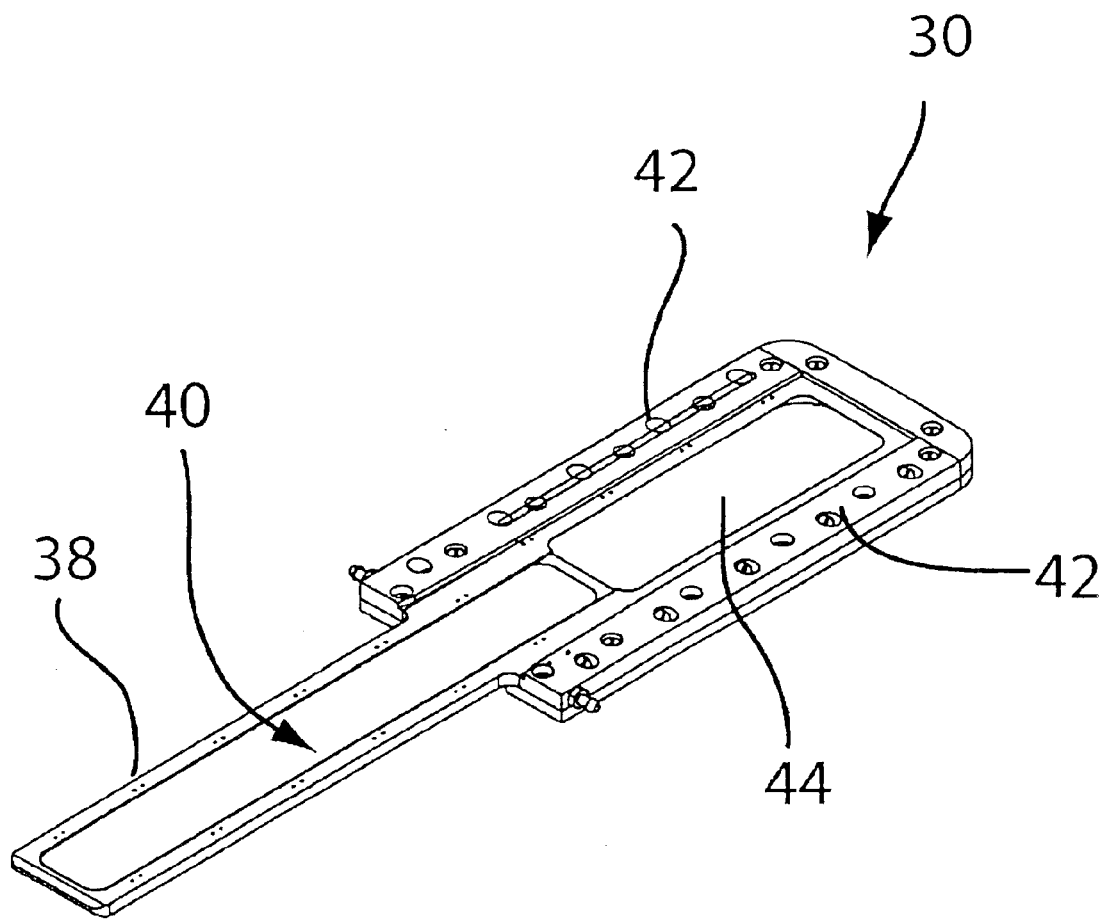
FIG. 4 is a perspective view of a slide conveyor according to the preferred embodiment of the invention.
Figure 5:
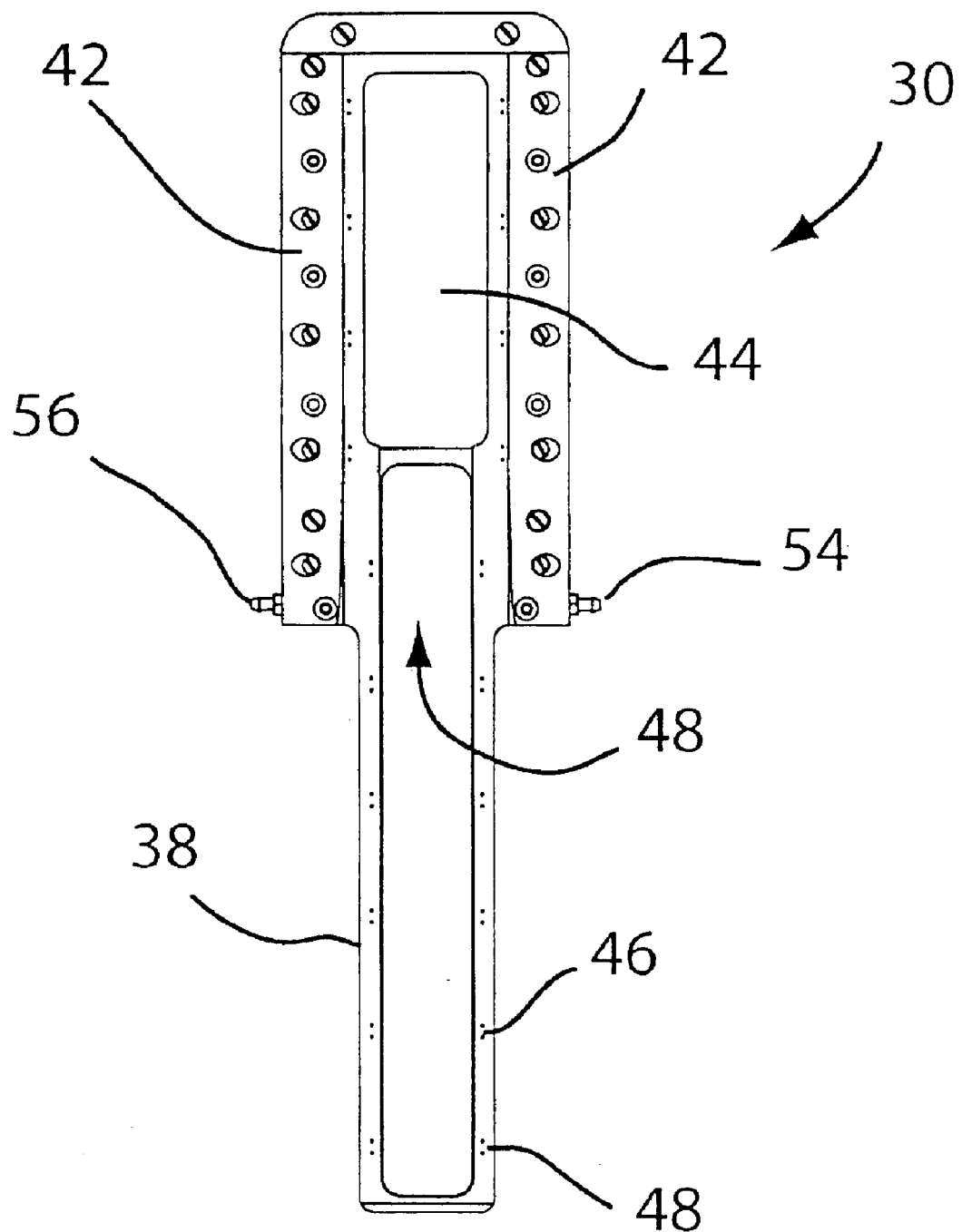
FIG. 5 is a top view of the conveyor of FIG. 4.
Figure 6:
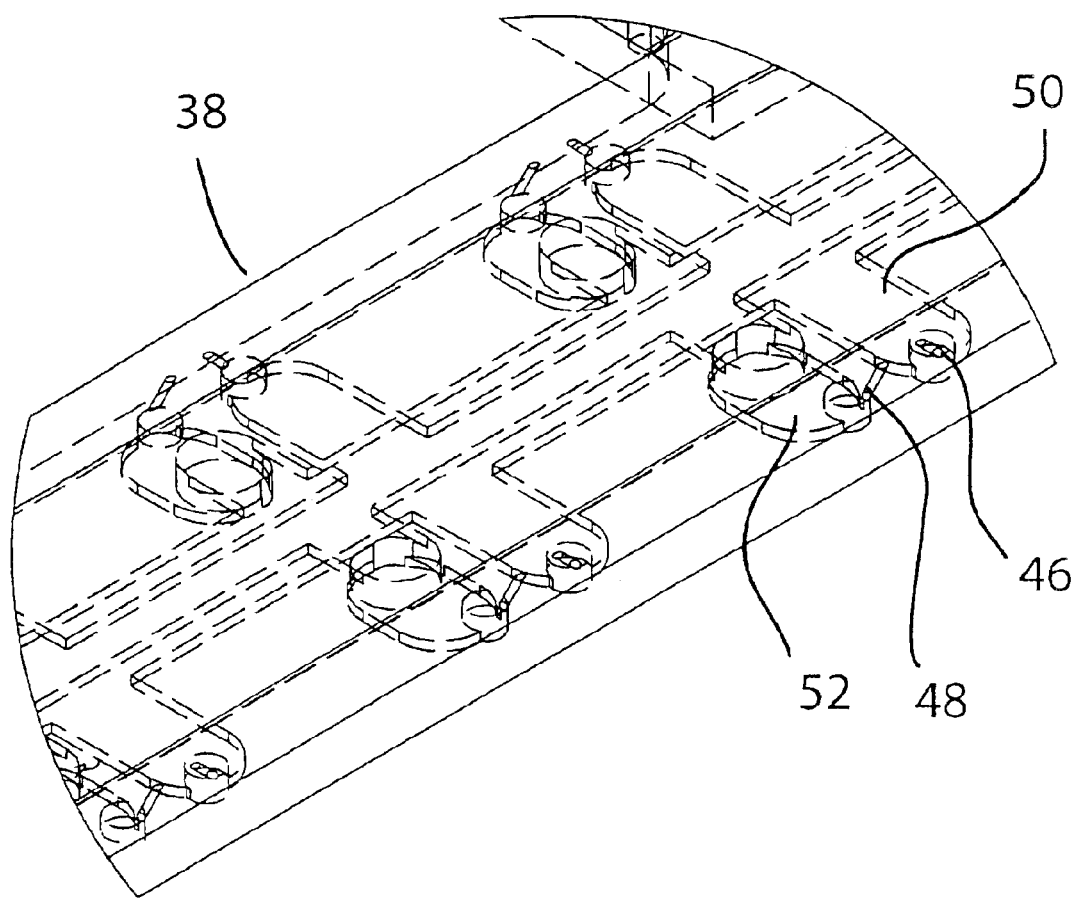
FIG. 6 is an enlarged view of a portion of the conveyor of FIG. 4, illustrating in phantom line plenums incorporated into the conveyor to provide air to the nozzles distributed along the edges of the runway in the conveyor.

According to the invention, as illustrated in the separate views of FIGS. 4 and 5, the conveyor 30 consists essentially of an air bearing runway 40 defined by the distal tongue 38 and by two lateral flanges 42 provided for connecting the tongue rigidly to the stage carriage 26. The proximal end of the runway 40 includes an open (or transparent) window 44 over which the slide of interest is placed for processing. Accordingly, the window 44 is appropriately sized to permit a full optical scan of the slide. The longitudinal sides of the runway are equipped with sets of air nozzles 46,48 capable of producing a uniform flow of air in either longitudinal direction. Accordingly, each set of nozzles includes at least one nozzle 46 set at an angle toward the magazine 14 and at least one other nozzle 48 set at an angle toward the carriage 26. As shown in the partial view of FIG. 6, pressurized air is provided to all nozzles 46 through a plenum 50 (shown in phantom line) on the top side of the tongue 38 and of the flanges 42, while a separate plenum 52 on the bottom side is used to feed air to all nozzles 48. Separate inlet ports 54 and 56 are provided to alternatively feed pressurized air to plenum 50 or 52, respectively. As is well understood in the art, suitable feed lines, control valves and corresponding control mechanisms and software are provided to pressurize either plenum 50 or 52 from a conventional compressor to move a slide toward or away from the magazine 14.

The orifices of nozzles 46,48 are sized such that, for a given air pressure in the corresponding plenums 50,52, a sufficient air flow is produced to suspend and move the glass slide longitudinally along the runway 40. This is achieved by an air flow that is also substantially uniform along the span of the runway irrespective of the position of the slide, so that the slide is able to glide over the air bearing produced by the nozzles without materially affecting the air flow out of the underlying nozzles. If the orifices in the nozzles are too large, the runway portion not covered by the slide will produce a vertical air barrier counteracting the motion of the slide. For smaller orifice sizes, once the slide is suspended, the air flow out of each nozzle is determined only by the pressure in the corresponding plenum and is not affected by the position of the slide. Therefore, this condition is optimal for the invention and the nozzles should be judiciously selected to produce the conditions described above. It is also clear that uniformly spaced nozzles produce a more uniform air bearing, which is much preferred.

It is noted that the precise angle of the air flow from the nozzles is not critical because any angle will include both an upward vertical component required to suspend the slide and a horizontal (longitudinal) component required to translate the slide. On the other hand, it is clear that angles approaching the vertical direction will produce very slow gliding motion while angles approaching horizontal flow will produce very little lift, which are both undesirable conditions.

I found that an angle of about 45 degrees with respect to vertical using 0.5-mm nozzles spaced about 18 mm apart on both sides of the runway produces a very consistent lift and smooth translation of a conventional glass slide (1"×3"— about 2.5 mm×7.5 mm×1.0 mm—weighing approximately 4.5 grams) operating at a plenum pressure of about 0.65 atmospheres above ambient.

Figure 7:
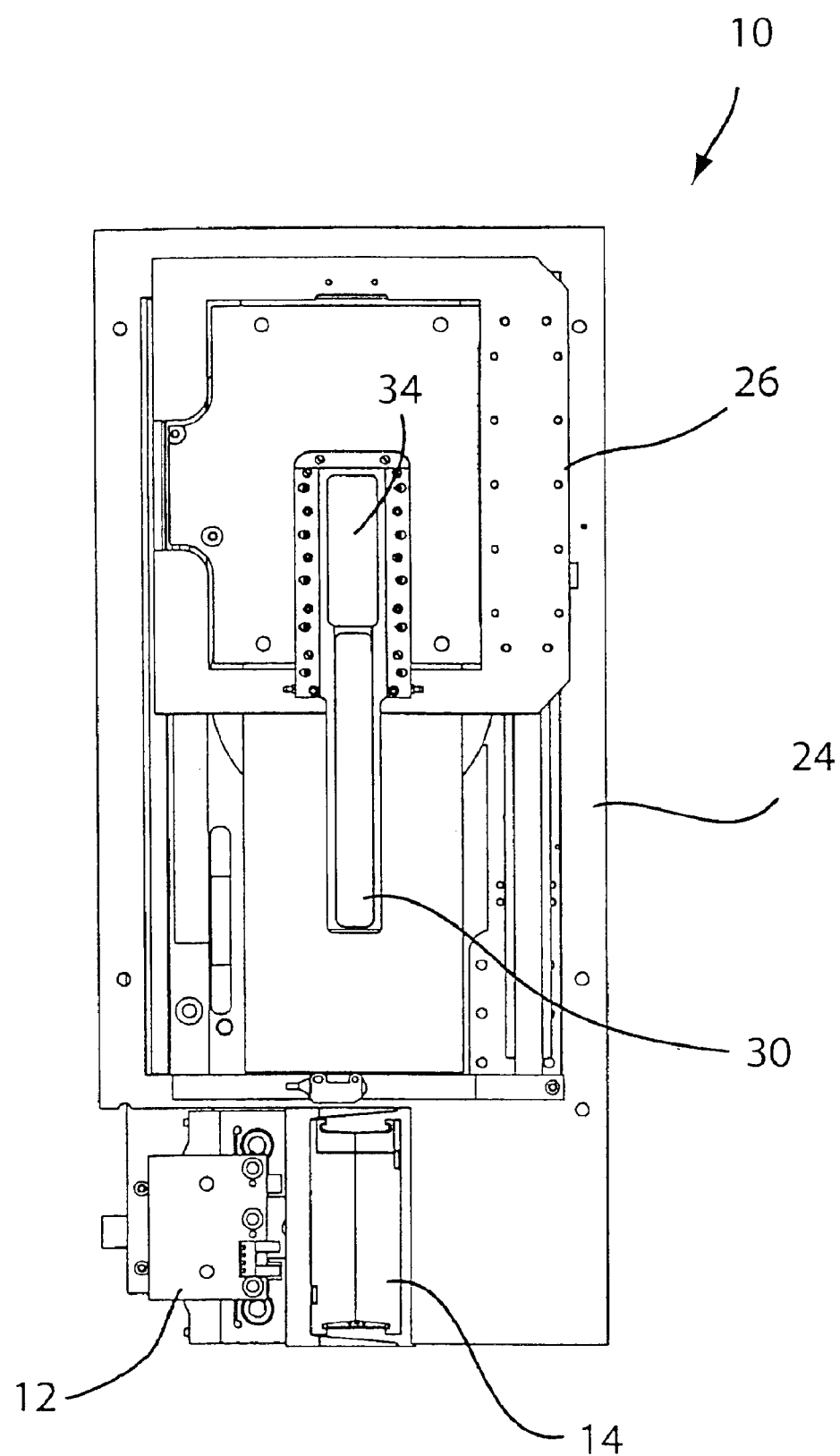
FIG. 7 is a top view of the feeder of FIG. 1 showing a slide lying over a transparent window for image processing after translation to the proximal end of the conveyor.

In operation, a magazine 14 loaded with slides 34 is placed either manually or automatically on the shelf 16 of the elevator 12 for sequential retrieval and processing. At each vertical position of the elevator (and correspondingly of the magazine), the stage carriage 26 is moved from its proximal position, illustrated in FIG. 1, to its distal position wherein the tongue 38 of the conveyor 30 is placed under the slide of interest, as illustrated in the side view of FIG. 3. As soon as the carriage reaches its distal position, the elevator is adjusted slightly to allow the slide to rest on the tongue 38. Then, the air flow to the plenum 50 and the nozzles 48 is initiated to lift the slide over the tongue and urge it toward the opposite end of the conveyor contained, in part, by the walls of the magazine. As soon as the slide reaches the window area of the runway, the carriage 26 can be moved back toward it proximal position as illustrated in the top view of FIG. 7, preferably at a speed that enables the carriage to reach its proximal end location as rapidly as possible. The air flow is interrupted and the slide is allowed to rest on the window 44 for processing. Then the procedure is reversed by pressurizing plenum 48 and beginning to move the carriage 26 toward the magazine 14 substantially at the same time, so that the slide 34 is again lifted and moved by the air flow out of the nozzles 46 toward the distal end of the tongue 38. Upon arrival of the tongue back into the slide slot in the magazine and the preferably rapid subsequent arrival of the slide 34 at the distal end of the tongue, the air flow is interrupted and the slide is released and deposited in its magazine slot. The tongue 38 is then extracted from the slot by the motion of the carriage and the elevator is moved to a different vertical position where the cycle is repeated for a new slide.

Figure 8:
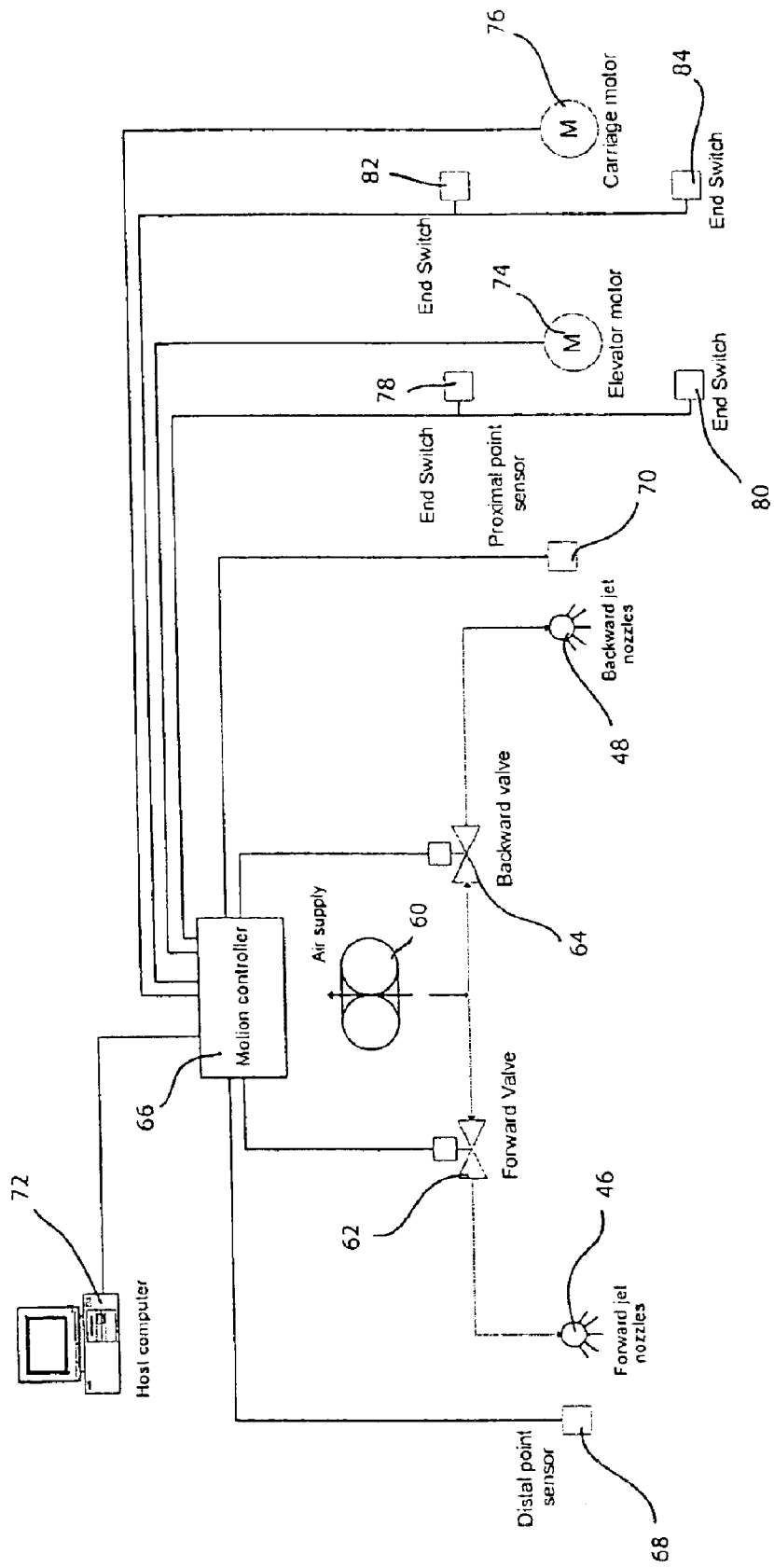
FIG. 8 is a schematic illustration of an air-flow control system suitable to practice the invention.

FIG. 8 illustrates a control system suitable to practice the invention. An 8 to 10-psig air supply 60 is used to provide air flow to the nozzles 46,48 alternatively through corresponding control valves 62,64. The valves are actuated by a motion controller 66 as a function of the position of the slide on the runway of the conveyor as determined by sensors 68,70 located at the two ends of the runway. A computer 72 with suitable control software is used to activate the valves as needed to move the slide between the two ends of the runway. The computer and motion controller are also used in conventional manner to change the position of the slide magazine and to move the carriage with motor 74,76 and end switches 78–84.

Figure 9:
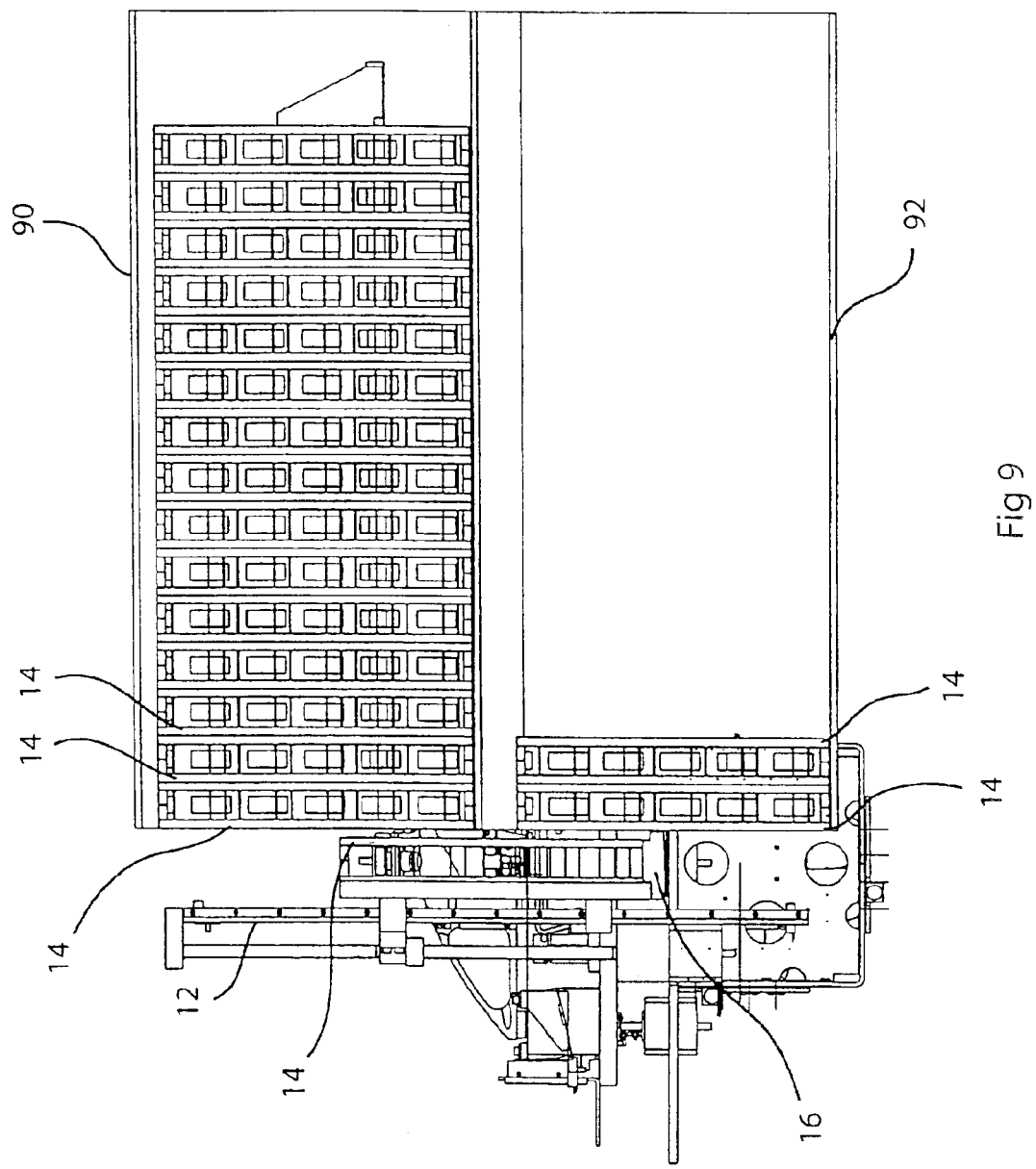
FIG. 9 is a front elevational view illustrating the feeder of the invention wherein the elevator is coupled to a mechanism capable of automatically engaging a plurality of magazines sequentially for processing a large number of slides.

Thus, a method and apparatus have been described that enable the smooth and rapid transport of a glass slide from a storage magazine to the stage of a microscope for digital is imaging. The invention utilizes a very small number of moving parts, thereby reducing production and maintenance costs and minimizing malfunctions. The system described herein has shown to be capable of processing slides sequentially at a rate of one slide every six seconds. By adding multiple magazines coupled to the elevator, as illustrated in FIG. 9, it is expected that the system will be able to process 720 slides continuously in a period of about 12 hours without the need to change magazines. The magazines are sequentially moved automatically from a first shelf 90 to the elevator 12 for processing, and then to a second shelf 92. Both shelves are preferably removable, so that the an entire set of magazines stored in a shelf may be processed, removed from the equipment, and replaced with another shelf.

Figure 10:
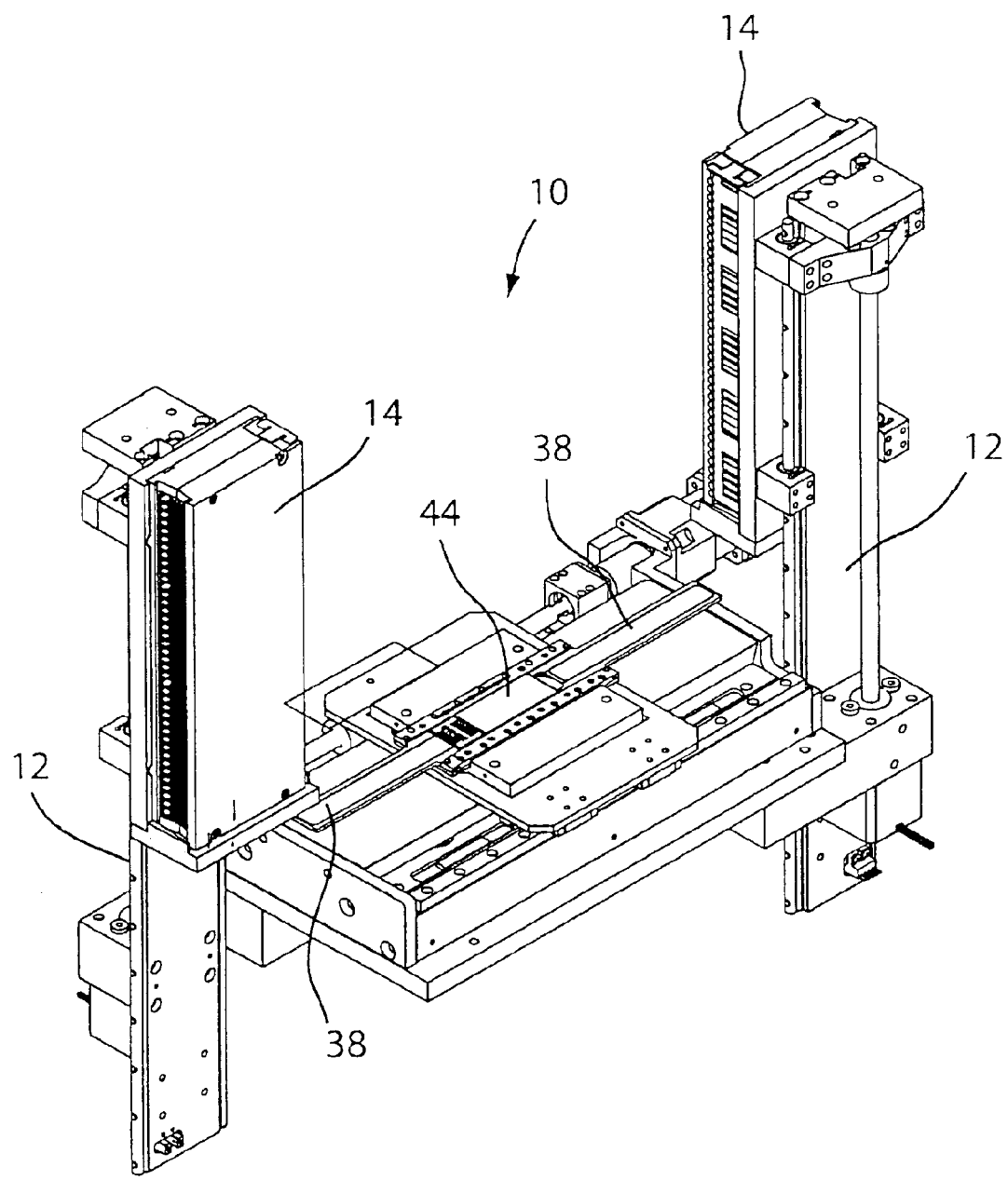
FIG. 10 is a view illustrating the feeder of the invention in use to move slides from one storage magazine to another storage magazine.

While the invention has been shown and described herein in what is believed to be the most practical and preferred embodiments with reference to a microscope, it is recognized that it is applicable to other optical instruments. For example, the invention could be used to move slides from one magazine to another. Similarly, it could be used to move slides from a magazine to a processing window, as discussed above, and then to another storage magazine, as illustrated in FIG. 10. Also, the invention discloses a linear runway, but it is clear that a curved horizontal runway could be implemented as well using appropriately placed nozzles that provide the air bearing and thrust required to move the slides; if necessary, lateral guides could be used to contain the slide as it moves along the curved path.

Figure 11:
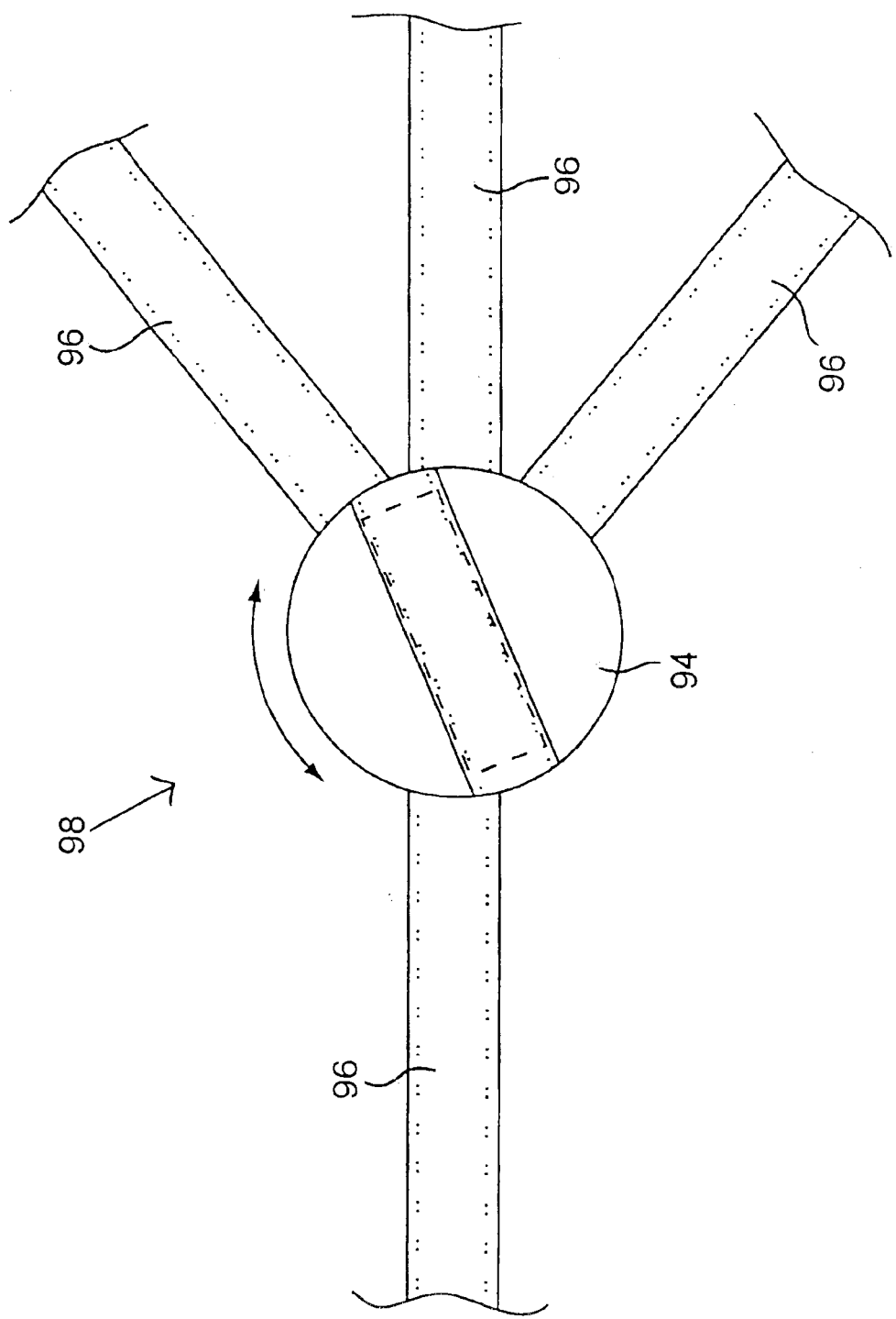
FIG. 11 is a view illustrating the feeder of the invention wherein the runway includes a turntable for alternatively directing the slide toward one of a plurality of end destinations.

The same concept could be used advantageously in a system with multiple destinations and a transfer mechanism, such as a rotating turntable 94, at the intersection of corresponding paths 96 in the runway 98, as illustrated in FIG. 11. In such a case, the turntable could either be treated as an intermediate destination where the slide is deposited, rotated toward the desired path, and floated again for transport in that direction; or it could be kept afloat while the turntable turns to the desired end direction. A bi-directional system of air nozzles as described above for the runway of the invention could also be used to transport and land, if desired, the slides over the turntable.

Accordingly, it is understood that departures can be made within the scope of the invention, which is not to be limited to the details disclosed herein but is to be accorded the full scope of the claims so as to embrace any and all equivalent methods and products.

I claim:

1. A slide feeder for moving a slide from a first location to a second location, comprising:
    a runway structure having a first end adapted to reach under said slide at said first location and a second end adapted to reach said second location;
    a first plurality of nozzles associated with the runway structure and directing a first fluid flow along the runway structure in a first direction having an upward vertical component and a horizontal component away from said first end of the runway structure;
    a second plurality of nozzles associated with the runway structure and directing a second fluid flow along the runway structure in a second direction having an upward vertical component and a horizontal component away from said second end of the runway structure; and
    means for alternatively activating said first and second fluid flows.

2. The slide feeder of claim 1, further comprising a first magazine with multiple, vertically stacked slots, each slot adapted to receive said slide, and wherein said first end of the runway structure is adapted to fit under the slide when the slide is located in one of said slots.

3. The slide feeder of claim 2, wherein said runway structure is mounted on a sample stage of an optical instrument, and said feeder includes a mechanism to move said second end of the runway structure to said second location for alignment with an objective of the instrument.

4. The slide feeder of claim 1, wherein said first and second pluralities of nozzles are uniformly spaced apart along side edges of the runway structure.

5. The slide feeder of claim 1, wherein said first and second directions of the fluid flows are at approximately 45 degrees from vertical.

6. The slide feeder of claim 2, wherein said second location is a second magazine with multiple, vertically stacked slots, each slot adapted to receive said slide, and wherein said second end of the runway structure is adapted to fit under the slide when the slide is located in one of said slots of the second magazine.

7. The slide feeder of claim 2, further comprising an elevator for vertical translation of the first magazine so that said slots can be aligned with the first end of the runway structure.

8. The slide feeder of claim 3, further comprising a second magazine with multiple, vertically stacked slots, each slot adapted to receive said slide, and comprising a mechanism to replace said first magazine with said second magazine.

9. The slide feeder of claim 1, wherein said runway structure includes a first plenum providing fluid to said first plurality of nozzles and a second plenum providing fluid to said second plurality of nozzles.

10. The slide feeder of claim 9, wherein said first and second pluralities of nozzles are uniformly spaced apart along side edges of the runway structure and said first and second directions of the fluid flows are at approximately 45 degrees from vertical.

11. The slide feeder of claim 1, wherein said runway structure further comprises a third end adapted to reach a third location, a third plurality of nozzles associated with the runway structure and directing a third fluid flow along the runway structure in a third direction having an upward vertical component and a horizontal component away from said third end of the runway, and means for directing the slide toward one of said first, second and third directions.

12. A method for moving a slide between a first location and a second location, comprising the following steps:
providing a runway structure having a first end adapted to reach under said slide at said first location and a second end adapted to reach said second location;
placing the first end of the runway structure under said slide when the slide is at said first location;
providing a first fluid flow along the runway structure in a first direction having an upward vertical component and a horizontal component away from said first end of the runway structure, thereby forming a first fluid bearing causing the slide to move to the second end of the runway structure; and
interrupting said first fluid flow to allow the slide to be landed at the second end of the runway structure.

13. The method of claim 12, further including the steps of moving the slide from said second end back to said first end of the runway structure by:
providing a second fluid flow along the runway structure in a second direction having an upward vertical component and a horizontal component away from said second end of the runway structure, thereby forming a second fluid bearing causing the slide to move to the first end of the runway structure; and
interrupting said second fluid flow to allow the slide to be landed at the first end of the runway structure.

14. The method of claim 13, further including the steps of providing a first magazine with multiple, vertically stacked slots, each slot adapted to receive said slide; and providing an elevator for vertical translation of the first magazine so that each of said slots can be aligned with the first end of the runway structure; wherein said first end of the runway structure is adapted to fit under the slide when the slide is located in one of said slots.

15. The method of claim 14, wherein said runway structure is mounted on a sample stage or an optical instrument, and the method further includes the step of providing a mechanism to move said second end of the runway structure to said second location for alignment with an objective of the instrument.

16. The method of claim 13, wherein said first and second fluid flows are provided using pluralities of nozzles uniformly spaced apart along side edges of the runway structure.

17. The method of claim 14, wherein said second location is a second magazine with multiple, vertically stacked slots, each slot adapted to receive said slide, and wherein said second end of the runway structure is adapted to fit under the slide when the slide is located in one of said slots of the second magazine.

18. The method of claim 14, further comprising the steps of providing a second magazine with multiple, vertically stacked slots, each slot adapted to receive said slide, and providing a mechanism to replace said first magazine with said second magazine.

19. The method of claim 13, wherein said runway structure includes a third end adapted to reach a third location from the first location, and, after said placing step, the method alternatively comprises the further steps of:
providing a third fluid flow along the runway structure in a third direction having an upward vertical component and a horizontal component toward said third end of the runway structure, thereby forming a third fluid bearing causing the slide to move to the third end of the runway structure; and
providing a fourth fluid flow along the runway structure in a fourth direction having an upward vertical component and a horizontal component away from said third end of the runway structure, thereby forming a fourth fluid bearing causing the slide to move away from the third end of the runway structure; and
providing means for directing the slide toward one of said first, second and third directions.

20. A slide feeder for moving a slide from a slot in a storage magazine to a stage of a microscope and back, comprising:
a magazine with multiple, vertically stacked slots, each slot adapted to receive a slide;
an elevator for vertical translation of the magazine so that said slots can be aligned with the slide feeder;
a runway structure having a first end adapted to reach under said slide in the slot of the magazine and a second end including a window for processing the slide in the stage of the microscope;
a carriage for moving the runway structure from a distal position wherein said first end thereof is placed under the slide to a proximal position wherein the window can be aligned with an objective of the microscope;
a first plurality of nozzles associated with the runway structure and directing a first air flow along the runway structure in a first direction having an upward vertical component and a horizontal component away from said first end of the runway structure;
a second plurality of nozzles associated with the runway structure and directing a second air flow along the runway structure in a second direction having an upward vertical component and a horizontal component away from said second end of the runway structure; and
means for alternatively activating said first and second air flows.

21. The slide feeder of claim 20, wherein said first and second pluralities of nozzles are uniformly spaced apart along side edges of the runway structure.

* * * * *